United States Patent

Karasawa et al.

Patent Number: 4,965,064
Date of Patent: Oct. 23, 1990

[54] PHEOPHORBIDE DERIVATIVES

[75] Inventors: Michito Karasawa, Settsu; Mari Uchimoto, Higashiosaka; Hirofumi Kawabe, Tokyo; Takuzo Otani, Sakai; Katsuo Aizawa, Yokohama, all of Japan

[73] Assignee: Hamari Chemicals, Ltd., Osaka, Japan

[21] Appl. No.: 285,106

[22] Filed: Dec. 15, 1988

[30] Foreign Application Priority Data

Dec. 21, 1987 [JP] Japan .................. 62-325083
Mar. 28, 1988 [JP] Japan .................. 63-75291

[51] Int. Cl.$^5$ .................. C07D 257/00; A61K 31/40; A61K 49/00
[52] U.S. Cl. ........................ 424/9; 514/410; 540/145
[58] Field of Search ............... 540/145; 514/183, 410; 424/9

[56] References Cited

U.S. PATENT DOCUMENTS 4,849,207 7/1929 Sakata et al. .................. 540/145

OTHER PUBLICATIONS

Dougherty, Photochem. and Photobiology, CD. pp. 879-889, 1987.
Gomer et al, Cancer Research, 39, 146-151, Jan. 1979.

Primary Examiner—Mukund J. Shah
Assistant Examiner—E. C. Ward
Attorney, Agent, or Firm—Burgess, Ryan & Wayne

[57] ABSTRACT

Novel pheophorbide derivatives of the general formula:

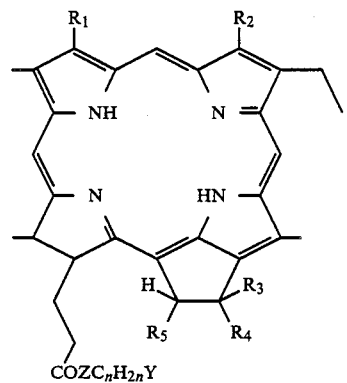

[wherein Z is O or NH; n is an integer of 1 to 6; Y is $NR'R''$ or

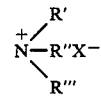

wherein R', R" and R''' are the same or different or each represents a $C_1$ to $C_4$ lower alkyl group; $X^-$ is a halogen or organic acid ion); $R_1$ is an ethenyl group; $C_1$ to $C_4$ lower alkyl group or

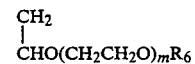

(wherein m is an integer of 0 to 6; $R_6$ is H or a $C_1$ to $C_4$ lower alkyl group); $R_2$ is $CH_3$, CHO or $CH_2OH$; either of $R_3$ and $R_4$ is H, with the other being OH, or both of them combine to represent =O; $R_5$ is H or $CO_2CH_3$) are provided.

When administered to a cancer-carrying animal, the derivatives accumulate specifically in cancer tissues and emit characteristic fluorescent spectrum under irradiation of light, which enables one to detect the cancer tissues.

4 Claims, No Drawings

PHEOPHORBIDE DERIVATIVES

This invention relates to novel pheophorbide derivatives that are usable in the diagnosis and therapy of cancer.

It is well known that the so-called photodynamic diagnosis and therapy, which comprises administering intravenously a photosensitive substance showing affinity to cancer cells and irradiating lesions with laser light after the elapse of a suitable length of time to conduct diagnosis and treatment of cancer tissues, is effective for the diagnosis and therapy of certain kinds of cancer (T. Dougherty; "Porphyrin Localization and Treatment of Tumors", pp. 75–87. D. R. Doiron and G. G. Gomer ed. Alan R. Liss. Inc., New York (1984)).

As the photosensitive substance for this purpose, there have heretofore been used porphyrins inclusive of hematoporphyrin (hereinafter referred to briefly as "HP"), particularly hematoporphyrin derivatives (hereinafter referred to briefly as "HpD") which can be produced by treating HP with sulfuric acid in acetic acid and carrying out alkali hydrolysis, followed by neutralization.

On the other hand, Rai et al. produced water-soluble pheophorbides by converting pheophorbide to its ethylenediamine hydrochloride (The Japanese Patent Application Laid-Open No. 981/1983), whereupon the ethylene diamine hydrochloride of pheophorbide is intended to be used as a bactericide.

Nevertheless, difficulties are encountered in producing HP with a high degree of purity (D. Dolphin ed. "The Prophyrins" vol. 1, pp. 297–298. Academic Press Inc. (1978)). In addition, HpD produced with use of such HP is known to be a mixture consisting of several kinds of porphyrin, and some postulated structures have only been proposed for the active form itself.

HP, after intravenous administration, is furthermore said to be incorporated into not only cancer tissues but also healthy tissues, particularly the liver in large quantities.

These constitute great obstacles in the clinical application of HP.

The present inventors, after extensive search for a photosensitive substance having affinity specific to cancer cells and showing a higher level of safety, found that amine derivatives of pheophorbide and their quaternary ammonium salts, which belong to analogs of porphyrins and are derived from chlorophyll of plant origin being known to exhibit photosensitivity, display enhanced affinity to cancer cells, and this finding has culminated into this invention.

This invention is concerned with pheophorbide derivatives represented by the general formula:

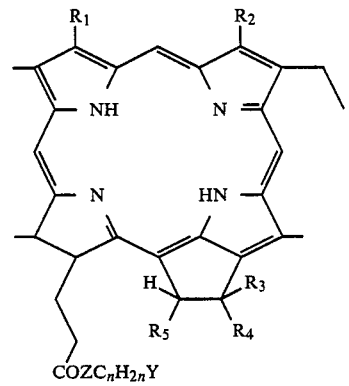

wherein Z is O or NH; n is an integer of 1 to 6; Y is NR'R" or

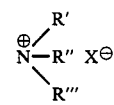

(wherein R', R" and R''' are the same or different from each other and each represents a $C_1$ to $C_4$ lower alkyl group and $X^\ominus$ is a halogen ion or organic acid ion); $R_1$ is a ethenyl or $C_1$ to $C_4$ lower alkyl group or

(wherein m is an integer of 0 to 6 and $R_6$ is H or a $C_1$ to $C_4$ lower alkyl group); $R_2$ is $CH_3$, CHO or $CH_2OH$; either of $R_3$ and $R_4$ is H, with the other being OH, or both of them combine to represent =O; $R_5$ is H or $CO_2CH_3$).

The $C_1$ to $C_4$ lower alkyl group represented by $R_1$, R', R", R''' and $R_6$ is preferably methyl, ethyl or n-propyl group. Preferred examples of the halogen ion represented by $X^\ominus$ include chlorine, bromine and iodine ions, while preferred examples of the organic acid ion shown by the same are ions such as acetic acid and p-toluenesulfonic acid ions.

By way of example, the pathway of synthesizing the pheophorbide derivatives of the present invention may be exemplified in the following:

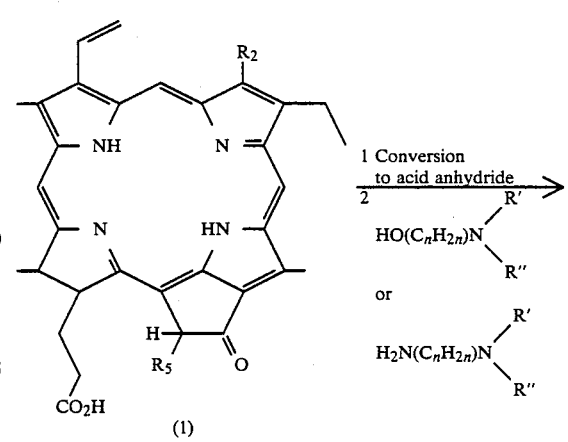

-continued

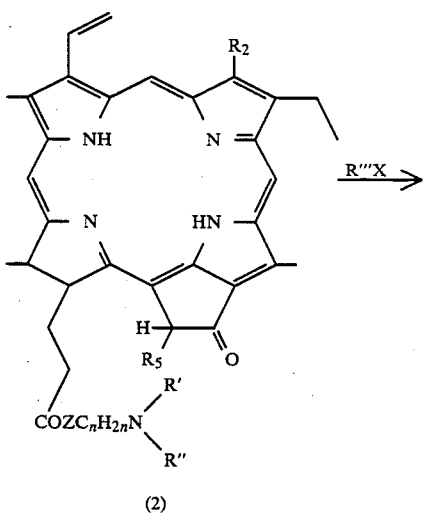

(2)

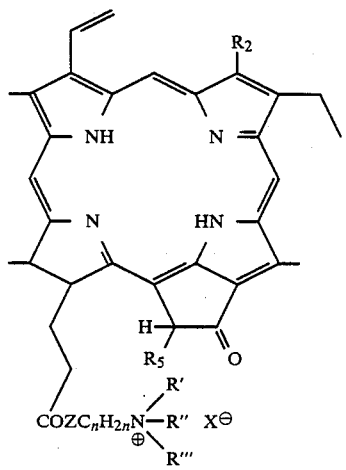

The compound of the present invention as represented by the formula (3) can be produced, for example, by the following procedure:

One of pheophorbides represented by the formula (1) is reacted with an acid anhydride converting agent in the presence of an acid capturing agent in a solvent to convert to an acid anhydride form, which is then reacted with a compound represented by the general formula

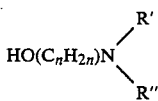

(In the respective formulae to be given below, each sign is understood to be as defined hereinbefore) or

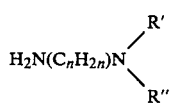

to give a compound of the general formula (2).

As the solvent being usable in this reaction, there are used anhydrous tetrahydrofuran, dioxane, ethyl acetate, methylene chloride, etc., with methylene chloride being preferable.

As the acid capturing agent, there are normally utilized triethylamine and tributylamine.

As the acid anhydride converting agent, use is made of acid chlorides and alkyl chloroformates, with pivaloyl chloride being preferred.

The reaction temperature and the reaction time can be suitably selected, but it is recommended to avoid extremely high temperatures, because these are liable to cause undesirable side reactions.

When methylene chloride is used as a solvent and triethylamine employed as a base, for example, the acid anhydride conversion reaction with pivaloyl chloride can be allowed to go to conclusion under ice-cooling for several minutes to 6 hours, and the subsequent esterification or amidation reaction can be brought to completion at room temperature for several to 24 hours.

The compounds of the formula (2) can be reacted with a lower alkyl halide R'''X in the presence or absence of solvent to give the compounds of the formula (3).

The desirable solvent which can be used in this reaction includes methylene chloride, chloroform, ethylene dichloride, benzene and the like. The reaction temperature and the reaction time can be suitably selected, and the reaction normally goes to completion at 0° to 100° C. for several minutes to several hours.

When benzene is used as solvent, for example, the reaction goes to completion at 20° to 30° C. for 30 minutes to 1 hour.

The compounds of the formula (3) can be adsorbed onto a suitable anion exchange resin and then eluted therefrom with an eluting solution containing an appropriate anion to exchange the halogen atom with the corresponding anion.

Also, the compounds of this invention as represented by the formula (5) can be produced by the following procedure:

A compound of the formula (2) is reacted with a suitable reducing agent such as sodium borohydride to convert to a compound of the formula (4), which is then subjected to reaction with a lower alkyl halide in a manner similar to the previously described step of (2)→(3) to give a compound (5).

Furthermore, the compounds of the formula (9) according to this invention can be obtained by the following procedure:

A compound of the formula (1) is converted to its hydrogen bromide adduct with a hydrogen bromide-acetic acid solution in the presence or absence of solvent, and the adduct is reacted with a compound represented by the formula HO(CH$_2$CH$_2$O)$_m$R$_6$, whereupon the resulting compound of the formula (6) is hydrolyzed to give a compound of the formula (7).

Subsequently, a compound of the formula (7) is allowed to undergo condensation with a compound represented by the formula

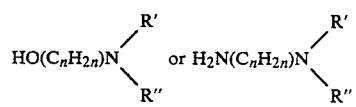

to give a compound of the formula (8), which is then reacted with a lower alkyl halide in a manner similar to the step of (2)→(3) to produce a compound (9).

The concentration of hydrogen bromide in the above-described hydrogen bromide-acetic acid solution is not specifically restricted, but normally ranges preferably from 25 to 30%. In the reaction with a compound represented by the general formula $HO(CH_2CH_2O)_m R_6$ or

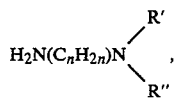

the reaction temperature and the reaction time can be suitably selected, and though the reaction goes to completion at 0° to 150° C. for 5 minutes to 5 hours, it normally is carried out preferably at a temperature in the neighborhood of 80° C. for about 2 hours.

In the above-described hydrolysis reaction, acid hydrolysis is normally preferred, whereby as the acid being usable in the reaction, there are employed mineral acids, such as hydrochloric acid and sulfuric acid, and organic acids, such as acetic acid and p-toluenesulfonic acid. In this reaction, the reaction temperature and the reaction time can be suitably selected, and the reaction ordinarily goes to conclusion at 0° to 150° C. for 5 minutes to 48 hours. For example, the reaction involving the use of sulfuric acid is brought to completion at 25° to 30° C. for 1 hour.

These reactions, i.e. esterification or amidation reaction, hydrogenation reaction, etherification reaction and hydrolysis reaction, may be employed independently of each other or can be used in suitable combinations thereof.

The post-reaction treatment and purification of these novel pheophorbide derivatives are conducted by means of ordinary procedures, such as extraction, recrystallization, and column chromatography.

The group of the compounds according to this invention can offer the following characteristic features in the diagnosis and therapy of cancer:

That is to say, the group of the compounds according to this invention, after given intravenously to cancer-carrying animals, accumulates specifically in cancer tissues and emits a fluorescent spectrum characteristic of this compound group when irradiated with light of an appropriate wavelength. This enables the mere measurement of such fluorescent spectra to determine the size and location of cancer tissues.

When irradiated with laser light of a suitable wavelength, on the other hand, a group of the compounds according to this invention can generate a singlet oxygen which exhibits cell killing action, and this permits the compound group to force cancer tissues alone to selective necrosis without inflicting any damamge to healthy tissues.

As a method of administration for the group of the compounds according to this invention, use can be made of various methods, and the compounds can be applied, for example, intravenously, subcutaneously, intraperitoneally, orally and intrarectally.

With reference to their dosages, the compounds are normally administered to human adults in the single dose of 0.1 to 350 mg, but the doses are not limited to such a range, being varied with the type of management or therapy.

Described in the following are the experiment example and examples to illustrate this invention in detail, but this invention is not intended to be limited to such description.

Experimental Example

The pheophorbide derivatives according to this invention were tested for their affinity to cancer tissues by the following method while using mice transplanted with cancer cells.

Experimental Method

Three-weeks aged mice of the Balb/c strain were transplanted subcutaneously with mouse kidney fibrosarcoma (MKSA) cells ($1 \times 10^7$ cells).

2 to 3 weeks after transplantation, each of the test samples was given to mice into the tail veint at a dose of 20 mg per kg of mouse body weight. 24 hours after the administration, cancer cells and organs were removed and excised, and measurements were taken of fluorescence characteristic of the compounds that had accumulated in the respective tissues by means of the endoscopic diganosis system using an excimer dye-laser (M. Aizawa et al., Journal of Laser Medical Association of Japan (*Rehzah Igakukaishi*), vol. 5, pp. 63–68 (1984)).

| [Test Samples] | |
|---|---|
| No. | Name of Compound |
| 1 | 2-Ethenyl-4-1,3,5,8-tetramethyl-9-desoxo-9-hydroxy-10-methoxycarbonyl-7-[2-(2-dimethylaminoethyloxy)carbonylethyl]-phorbin |
| 2 | 2-Ethenyl-4-ethyl-1,3,5,8-tetramethyl-9-desoxo-9-hydroxy-10-methoxycarbonyl-7-[2-(2-trimethylammonioethyloxy)carbonylethyl]phorbin.iodide |
| 3 | 2-Ethenyl-4-ethyl-1,3,5,8-tetramethyl-9-desoxo-9-hydroxy-10-methoxycarbonyl-7-[2-(2-trimethylammoniopropyloxy)carbonylethyl]-phorbin.iodide |
| 4 | 2-Ethenyl-4-ethyl-1,3,58-tetramethyl-9-oxo-10-desmethoxycarbonyl-10(H)-7-[2-(2-trimethylammonioethyloxy)carbonylethyl]-phorbin.iodide |
| 5 | 2-Desethenyl-2-(1-methoxyethyl)-4-ethyl-1,3,5,8-tetramethyl-9-desoxo-9-hydroxy-10-methoxycarbonyl-7-[2-(2-trimethylammonioethyloxy)carbonylethyl]-phorbin.iodide |
| 6 | 2-Desethenyl-2-(1-(2-(2-hydroxyethyloxy)ethyloxy)-ethyl)-4-ethyl-1,3,5,8-tetramethyl-9-oxo-10-desmethoxycarbonyl-10(2H)-7-[2-(2-trimethylammonioethyloxy)carbonylethyl]-phorbin.iodide |

Results

Shown in Table 1 are the amounts of fluorescence in cancer tissues and ratios of the amounts of fluorescence in cancer tissues to healthy tissues, as broken down by the respective test compounds. As is evident from the Table, the compounds according to this invention exhibit by far stronger affinity to cancer tissues than to healthy tissues.

| Test sample No. | Quantity of fluorescence each of the individual compounds in tumor tissue | Ratio of quantities of fluorescence in tumor tissue to normal healthy tissue | | | |
|---|---|---|---|---|---|
| | | Lung | Intestinum | Muscle | Skin |
| 1 | Not less than 5.85 | 0.16 | 0.28 | 0.27 | 0.24 |
| 2 | Not less than 7.73 | 0.12 | 0.23 | 0.21 | 0.62 |
| 3 | 4.98 | 0.41 | 0.19 | 0.14 | 0.37 |

-continued

| Test sample No. | Quantity of fluorescence each of the individual compounds in tumor tissue | Ratio of quantities of fluorescence in tumor tissue to normal healthy tissue | | | |
|---|---|---|---|---|---|
| | | Lung | Intestinum | Muscle | Skin |
| 4 | 5.44 | 0.23 | 0.35 | 0.40 | 0.65 |
| 5 | 5.78 | 0.29 | 0.67 | 0.30 | Not less than 1.51 |
| 6 | 5.47 | 0.33 | 0.71 | 0.59 | Not less than 1.76 |

EXAMPLE 1

Synthesis of 2-ethenyl-4-ethyl-1,3,5,8-tetramethyl-9-oxo-10-methoxycarbonyl-7-[2-(2-dimethylaminoethyloxy)carbonylethyl]-phorbin To a solution of 1200 mg of 2-ethenyl-4-ethyl-1,3,5,8-tetramethyl-9-oxo-10-methoxycarbonyl-phorbin-7-propionic acid in 100 ml of methylene chloride are added, under ice-cooling, 500 mg of triethylamine and 300 mg of pivaloyl chloride, and stirring is conducted at $-5°$ to $0°$ C. for 4 hours. 1.0 ml of N,N-dimethylethanolamine is added to the solution, followed by stirring at room temperature. The reaction solution is diluted with 500 ml of cold water, neutralized with a suitable quantity of acetic acid and then extracted three times with 300 ml of chloroform. The extracts are combined, washed six times with 500 ml of water, and dried over anhydrous sodium sulfate, followed by removal of solvent.

The resulting residue is chromatographed on a column of alumina (Merck, 500 g with activity V), and elution is effected with chloroform-methanol (100:1). The eluate is freed of solvent under vacuum to give 322 mg (24.2%) of 2-ethenyl-4-ethyl-1,3,5,8-tetramethyl-9-oxo-10-methoxycarbonyl-7-[2-(2-dimethylaminoethyloxy)carbonylethyl]-phorbin in the form of black crystals.

IR absorption spectrum (KBr, $cm^{-1}$): 3395, 2950, 2930, 2855, 2810, 2760, 1740, 1695, 1615.

Nuclear magnetic resonance spectrum (CDCl$_3$, δ ppm, TMS): 1.56 (t, 3H), 1.82(d,3H), 2.12(s,6H), 2.12 to 2.82 (m,6H), 3.03(s,3H), 3.32(s,3H), 3.46(q,2H), 3.64(s,3H), 3.89(s,3H), 3.82 to 4.64(m,4H), 6.00 to 6.24(m,2H), 6.26 (s,1H), 7.86(dd,1H), 8.56(s,1H), 9.15(s,1H), 9.32(s,1H), −196(br.s,1H).

EXAMPLE 2

Synthesis of 2-ethenyl-4-ethyl-1,3,5,8-tetramethyl-9-desoxy-9-hydroxy-10-methoxycarbonyl-7-[2-(2-dimethylaminoethyloxy)carbonylethyl]-phorbin A solution of 40 mg of sodium borohydride in 5 ml of cold methanol is added to a solution in 10 ml of methanol of 66 mg of 2-ethenyl-4-ethyl-1,3,5,8-tetramethyl-9-oxo-10-methoxycarbonyl-7-[2-(2-dimethylaminoethyloxy)carbonylethyl]-phorbin as produced in Example 1, followed by stirring at room temperature for 10 minutes. The reaction solution is diluted with 10 ml of cold water, treated with an appropriate volume of acetic acid to decompose the excessive sodium borohydride and extracted three times with 20 ml of chloroform. The combined organic layer is washed three times with 50 ml of water, dried over anhydrous sodium sulfate and freed of solvent under reduced pressure. The residue is chromatographed on a column of alumina (Merck, 50 g with activity V), and elution is performed with chloroform-methanol (100:1). The eluate is concentrated to give 54 mg (81.8%) of 2-ethenyl-4-ethyl-1,3,5,8-tetramethyl-9-desoxo-9-hydroxy-10-methoxycarbonyl-7-[2-(2-dimethylaminoethyloxy)carbonylethyl]-phorbin in the form of dark green crystals.

IR absorption spectrum (KBr, $cm^{-1}$): 3395, 2955, 2930, 2855, 2815, 2775, 1730, 1615.

Nuclear magnetic resonance spectrum (CDCl$_3$, δ ppm, TMS) −3.21(br.s,2H), 1.71(t,3H), 1.88(d,2H), 2.00,2.04 (each s,6:4,6H), 2.15 to 2.79(m,6H), 3.33(s,3H), 3.52 (s,3H), 3.58(s,3H), 3.43(m,4H), 3.88(s,3H), 4.36 to 4.80 (m,2H), 5.91 to 6.77(m,4H), 8.12(dd,1H), 8.89(s,1H), 9.56 (1H,s), 9.77(s,1H).

EXAMPLE 3

Synthesis of 2-ethenyl-4-ethyl-1,3,5,8-tetramethyl-9-oxo-10-methoxycarbonyl-7-[2-(3-dimethylaminopropyloxy)carbonylethyl]-phorbin 2-Ethenyl-4-ethyl-1,3,5,8-tetramethyl-9-oxo-10-methoxycarbonyl-phorbin-7-propionic acid is reacted with pivaloyl chloride in the same manner as described in Example 1, followed by treatment with N,N-dimethylaminopropanol to give 2-ethenyl-4-ethyl-1,3,5,8-tetramethyl-9-oxo-10-methoxycarbonyl-7-[2-(3-dimethylaminopropyloxy)carbonylethyl]-phorbin. Yield of 21.8%.

IR absorption spectrum (KBr, $cm^{-1}$); 3400, 2950, 2930, 2860, 2820, 2775, 1730, 1615

Nuclear magnetic resonance spectrum (CDCl$_3$, δ ppm, TMS): −1.97(br.s,1H), 1.57(t,3H), 1.81(d,3H), 2.11(s,6H), 2.10 to 2.82(m,6H), 3.04(s,3H), 3.33(s,3H), 3.49(q,2H), 3.60(s,3H), 3.86(s,3H), 3.49 to 4.66(m,6H), 6.01 to 6.23 (m,2H), 6.28(s,1H), 7.88(dd,1H), 8.54(s,1H), 9.17(s,1H), 9.30(s,1H).

EXAMPLE 4

Synthesis of 2-ethenyl-4-ethyl-1,3,5,8-tetramethyl-9-desoxo-9-hydroxy-10-methoxycarbonyl-7-[2-(3-dimethylaminopropyloxy)carbonylethyl]-phorbin 2-Ethenyl-4-ethyl-1,3,5,8-tetramethyl-9-oxo-10-methoxycarbonyl-7-[2-(3-dimethylaminopropyloxy)-carbonylethyl]-phorbin as produced in Example 3 is treated in the same manner as described in Example 2 to give 2-ethenyl-4-ethyl-1,3,5,8-tetramethyl-9-desoxo-9-hydroxy-10-methoxycarbonyl-7-[2-(3-dimethylaminopropyloxy)carbonylethyl]-phorbin. Yield of 85.3%.

IR absorption spectrum (KBr, $cm^{-1}$): 3395, 2955, 2910, 2855, 2735, 1735, 1700, 1615.

Nuclear magnetic resonance spectrum (CDCl$_3$, δ ppm, TMS): −3.20(br.s,1H), 1.71(t,3H), 1.88(d,3H), 1.97, 2.02 (each s,3.6H,2.4H), 2.06 to 2.82(m,6H), 3.35(s,3H), 3.52 (s,3H), 3.56(s,3H), 3.76(m,4H), 3.86(s,3H), 4.09 to 4.79 (m,4H), 5.88 to 6.77(m,4H), 8.14(dd,1H), 8.85(s,1H), 9.53 (s,1H), 9.77(s,1H).

EXAMPLE 5

Synthesis of 2-ethenyl-4-ethyl-1,3,5,8-tetramethyl-9-oxo-10-desmethoxycarbonyl-10(2H)-7-[2-(2-dimethylaminoethyloxy)carbonylethyl]-phorbin 2-Ethenyl-4-ethyl-1,3,5,8-tetramethyl-9-oxo-10-desmethoxycarbonyl-10(2H)-phorbin-7-propionic acid is treated in the same manner as described in Example 1 to give 2-ethenyl-4-ethyl-1,3,5,8-tetramethyl-9-oxo-10-desmethoxycarbonyl-10(2H)-7-[2-(2-dimethylaminoethyloxy)carbonylethyl]-phorbin. Yield of 38.2%.

IR absorption spectrum (KBr, cm$^{-1}$): 3400, 2950, 2920, 2855, 2820, 2760, 1730, 1690, 1620.

Nuclear magnetic resonance spectrum (CDCl$_3$, δ ppm, TMS): −1.88(br.s,2H), 1.52(t,3H), 1.74(d,3H), 2.10(s,6H), 2.20 to 2.78(m,6H), 2.94(s,3H), 3.24(s,3H), 3.35(q,2H), 3.42(s,3H), 4.02(t,3H), 3.97 to 4.56(m,2H), 4.89(dd,2H), 5.95(m,2H), 7.70(dd,1H), 8.35(s,1H), 8.92(s,1H), 9.02(s,1H).

EXAMPLE 6

Synthesis of 2-ethenyl-4-ethyl-1,3,5,8-tetramethyl-9-desoxo-9-hydroxy-10-desmethoxycarbonyl-10(2H)-7-[2-(2-dimethylaminoethyloxy)carbonylethyl]-phorbin 2-Ethenyl-4-ethyl-1,3,5,8-tetramethyl-9-oxo-10-desmethoxycarbonyl-10(2H)-7-[2-(2-dimethylaminoethyloxy)carbonylethyl]-phorbin as produced in Example 5 is treated in the same manner as described in Example 2 to give 2-ethenyl-4-ethyl-1,3,5,8-tetramethyl-9-desoxo-9-hydroxy-10-desmethoxycarbonyl-10(2H)-7-[2-(2-dimethylaminoethyloxy)carbonylethyl]-phorbin. Yield of 86.8%.

IR absorption spectrum (KBr, cm$^{-1}$); 3395, 2955, 2920, 2860, 2830, sh, 2780, 1735, 1619.

Nuclear magnetic resonance spectrum (CDCl$_3$, δ ppm, TMS): −3.20(br.s,2H), 1.71(t,3H), 1.80(d,3H), 2.03(s,6H), 2.10 to 2.88(m,6H), 3.33(s,3H), 3.48(s,6H), 3.64 to 4.06(m,4H), 4.29 to 4.73(m,2H), 5.06 to 5.42(m,2H), 6.18(m,3H), 8.10 (dd,1H), 8.80(s,1H), 9.47(s,1H), 9.74(s,1H).

EXAMPLE 7

Synthesis of 2-desethenyl-2-(1-methoxyethyl)-4-ethyl-1,3,5,8-tetramethyl-9-oxo-10-methoxycarbonyl-phorbin-7-propionic acid methyl ester In 10 ml of 25% hydrogen bromide acetic acid solution is dissolved 200 mg of 2-ethenyl-4-ethyl-1,3,5,8-tetramethyl-9-oxo-10-methoxycarbonyl-phorbin-7-propionic acid, followed by stirring at room temperature for 12 hours to allow the reaction to proceed. The reaction solution is concentrated to dryness under reduced pressure, and the residue is treated with 10 ml of methanol, followed by heating under reflux for 6 hours. The resulting solution is allowed to cool, diluted with 50 ml of methylene chloride and washed twice with 100 ml of water. Then the solution is dried over anhydrous sodium sulfate, and the solvent is removed by vacuum distillation. The residue is chromatographed on a column of alumina (Merck, 50 g with activity of II to III), with methylene chloride being used as the eluting solution, and the eluate is freed of solvent by vacuum distillation to give 140 mg of 2-desethenyl-2-(2-methoxyethyl)-4-ethyl-1,3,5,8-tetramethyl-9-oxo-10-methoxycarbonyl-phorbin-7-propionic acid methyl ester in the form of dark green crystals.

IR absorption spectrum (KBr, cm$^{-1}$): 3400, 2950, 2030, 2860, 1740, 1710, 1620.

Nuclear magnetic resonance spectrum (CDCl$_3$, δ ppm, TMS): −1.70(br.s.,2H), 1.65(t,3H), 1.80(d,3H), 2.13(d,3H), 2.37(m,4H), 3.23(s,3H), 3.41(s,3H), 3.56(s,6H), 3.60(s,3H) 3.89(s,3H), 4.00 to 4.63(m,2H), 5.80(m,1H), 6.18(s,1H), 8.51(s,1H), 9.33(s,1H), 9.62(s,1H).

EXAMPLE 8

Synthesis of 2-desethenyl-2-(1-methoxyethyl)-4-ethyl-1,3,5,8-tetramethyl-9-oxo-10-methoxycarbonyl-phorbin-7-propionic acid In 5 ml of 50% aqueous sulfuric acid solution is dissolved 50 mg of 2-desethenyl-2-(1-methoxyethyl)-4-ethyl-1,3,5,8-tetramethyl-9-oxo-10-methoxycarbonyl-phorbin-7-propionic acid methyl ester as produced in Example 7, and the solution is stirred at room temperature for 2 hours. The reaction solution is diluted with 50 ml of water and extracted three times with 20 ml of methylene chloride. The methylene chloride layers are combined, washed three times with 100 ml of water and dried over anhydrous sodium sulfate. The solvent is distilled off to give 36 mg of 2-desethenyl-2-(1-methoxyethyl)-4-ethyl-1,3,5,8-tetramethyl-9-oxo-10-methoxycarbonyl-phorbin-7-propionic acid in the form of dark green crystals.

IR absorption spectrum (KBr, cm$^{-1}$): 3400, 2955, 2830, 2960, 1700, 1690, 1605.

EXAMPLE 9

Synthesis of 2-desethenyl-2-(1-methoxyethyl)-4-ethyl-1,3,5,8-tetramethyl-9-oxo-10-methoxycarbonyl-7-[2-(2-dimethylaminoethyloxy)carbonylethyl]-phorbin 2-Desethenyl-2-(1-methoxyethyl)-4-ethyl-1,3,5,8-tetramethyl-9-oxo-10-methoxycarbonyl-phorbin-7-propionic acid as produced in Example 8 is treated in the same manner as described in Example 1 to give 2-desethenyl-2-(1-methoxyethyl)-4-ethyl-1,3,5,9-tetramethyl-9-oxo-10-methoxycarbonyl-7-[2-(2-dimethylaminoethyloxy)carbonylethyl]-phorbin. Yield of 20.5%.

IR absorption spectrum (KBr, cm$^{-1}$): 3400, 2950, 2820, 2860, 2830, 2775, 1730, 1695, 1615.

Nuclear magnetic resonance spectrum (CDCl$_3$, δ ppm, TMS): −1.76(br.s.,2H), 1.65(t,3H), 1.76(d,3H), 2.10(s,6H), 2.12(d,3H), 2.13 to 2.89 (m,6H), 3.22(s,3H), 3.38(s,3H), 3.58(s,6H), 3.75(q,2H), 3.78(s,3H), 4.03(m,2H), 4.18 to 4.64(m,2H), 5.85(m,1H), 6.20(s,1H), 8.51(s,1H), 9.33(s,1H), 9.63(s,1H).

EXAMPLE 10

Synthesis of 2-desethenyl-2-(1-1-methoxyethyl)-4-ethyl-1,3,5,8-tetramethyl-9-desoxo-9-hydroxy-10-methoxycarbonyl-7-[2-(2-dimethylaminoethyloxy)carbonylethyl]-phorbin 2-Desethenyl-2-(1-methoxyethyl)-4-ethyl-1,3,5,8-tetramethyl-9-oxo-10-methoxycarbonyl-7-[2-(2-dimethylaminoethyloxy)carbonylethyl]-phorbin as produced in Example 9 is treated in the same manner as described in Example 2 to give 2-desethenyl-2-(1-methoxyethyl)-4-ethyl-1,3,5,8-tetramethyl-9-desoxo-9- hydroxy-10-methoxycarbonyl-7-[2-(2-dimethylaminoethyloxy)carbonylethyl]-phorbin. Yield of 75.6%.

IR absorption spectrum (KBr, cm$^{-1}$): 3395, 2950, 2920, 2860, 2835, 2760, 1736, 1615.

Nuclear magnetic resonance spectrum (CDCl$_3$, δ ppm, TMS): −3.21(br.s,2H), 1.70(t,3H), 1.84(d,3H), 1.97(s,6H), 2.08(d,3H), 2.45(m,6H), 3.29(br.s,9H), 3.48(s,3H), 3.73 (m,4H), 3.85(s,3H), 4.27 to 4.76(m,2H), 6.13(m,3H), 6.58 (m,1H), 8.76(s,1H), 9.55(s,1H), 9.83(s,1H).

EXAMPLE 11

Synthesis of
2-desethenyl-2-(1-2(2-hydroxyethyloxy)ethyloxy)ethyl)-4-ethyl-1,3,5,8-tetramethyl-9-oxo-10-desmethoxycarbonyl-10(2H)-7-[2-(2-(2-hydroxyethyloxy)ethyloxy)carbonylethyl]-phorbin In the same manner as described in Example 7, 100 mg of 2-ethenyl-4-ethyl-1,3,5,8-tetramethyl-9-oxo-10-desmethoxycarbonyl-10(2H)-phorbin-7-propinionic acid is treated with hydrogen bromide acetic acid solution, and the resulting product is reacted with 5 ml of diethylene glycol. The same procedure as described in Example 7 is carried out to give 80 mg of 2-desethenyl-2-(1-(2-(2-hydroxyethyloxy)ethyloxy)ethyl)-4-ethyl-1,3,5,8-tetramethyl-9-oxo-10-desmethoxycarbonyl-10(2H)-7-[2-(2-(2-hydroxyethyloxy)ethyloxy)carbonylethyl]-phorbin in the form of dark green crystals.

IR absorption spectrum (KBr, cm$^{-1}$): 3450, 2960, 2930, 2870, 1740, 1680, 1620.

Nuclear magnetic resonance spectrum (CDCl$_3$, δ ppm, TMS): −1.83(br.s,2H), 1.67(t,3H), 1.81(1d,3H), 2.13(d,3H), 2.42(m,4H), 3.27(s,3H), 3.40(s,3H), 3.58(s,3H), 3.49(m,6H), 3.58(m,6H), 3.77(m,8H), 4.16 to 3.95(m,6H), 4.39(m,2H), 5.13(br.s,2H), 5.99(m,1H), 8.50(s,1H), 9.33(s,1H), 9.71(s,1H).

EXAMPLE 12

Synthesis of
2-desethnyl-2-(1-(2-(2-hydroxyethyloxy)ethyloxy)ethyl)-4-ethyl-1,3,5,8-tetramethyl-9-oxo-10-desmethoxycarbonyl-10(2H)-phorbin-7-propionic acid By following the same procedure as described in Example 8, 80 mg of 2-desethenyl-2-(1-(2-(2-hydroxyethyloxy)ethyloxy)ethyl)4-ethyl-1,3,5,8-tetramethyl-9-oxo-10-desmethoxycarbonyl-10(2H)-7-[2-(2-(2-hydroxyethyloxy)ethyloxy)carbonylethyl]-phorbin is treated to give 45 mg of 2-desethenyl-2-(1-(2-(2-hydroxyethyloxy)ethyloxy)ethyl-4-ethyl-1,3,5,8-tetramethyl-9-oxo-10-desmethoxycarbonyl-10(H)-phorbin-7-proppionic acid in the form of dark green crystals.

IR absorption spectrum (KBr, cm$^{-1}$): 3400, 2960, 2930, 2870, 1680, 1615.

EXAMPLE 13

Synthesis of
2-desethenyl-2-(1-(2-(2-hydroxyethyloxy)ethyloxy)ethyl)-4-ethyl-1,3,5,8-tetramethyl-9-oxo-10-desmethoxycarbonyl-10(2H)-7-[2-(2-dimethylaminoethyloxy)carbonylethyl]-phorbin By following the same procedure as described in Example 1,2-desethenyl-2-(1-(2-(2-hdyroxyethyloxy)ethyloxy)ethyl)-4-ethyl-1,3,5,8-tetramethyl-9-oxo-10-desmethoxycarbonyl-10(2H)phorbin-7-propionic acid as produced in Example 12 is treated to give 2-desethenyl-2-(1-(2-(2-hydroxyethyloxy)ethyloxy)ethyl)-4-ethyl-1,3,5,8-tetramethyl-9-oxo-10-desmethoxyxcarbonyl-10(2H)-7-(2-(2-diemthylaminoethyloxy)carbonylethyl]-phorbin. Yield of 18.5%.

IR absorption spectrum (KBr, cm$^{-1}$); 3390, 2950, 2920, 2855, 27770, 1730, 1695, 1720.

Nuclear magnetic resonance spectrum (CDCl$_3$, δ ppm, TMS): −1.74(br.s,2H), 1.64(t,3H), 1.73(d,3H), 2.11(s,6H), 2.12(d,3H), 2.15 to 2.88(m,6H), 3.21(s,3H), 3.36(s,3H), 3.58(s,3H), 3.70(m,10H), 3.76(s,3H), 4.03(m,2H), 4.18 to 4.64(m,2H), 5.10(dd,2H), 5.98(m,1H), 8.48(s,1H), 9.32 (s,1H), 9.64(s,1H).

EXAMPLE 14

Synthesis of
2-ethenyl-4-ethyl-1,3,5,8-tetramethyl-9-oxo-10-methoxycarbonyl-7-[2-(2-(-trimethylammonioethyloxy)carbonylethyl]-phorbin-iodide In 5 ml of benzne is dissolved 66 mg of 2-ethenyl-4-ethyl-1,3,5,8-tetramethyl-9-oxo-10-methoxycarbonyl-7-[2-(2-diemthylaminoethyloxy)carbonylethyl]-phorbin as produced example 1, and 0.1 ml of methyl iodide is added to the solution, followed by standing at room temperature for 1 hour. The crystals, which precipiate out, are washed with benzene and dried to give 58 mg of 2-ethenyl-4-ethyl-1,3,5,8-tetramethyl-9-oxo-10-methoxycarbonyl-7-[2-(2-trimethylammonioethyloxy)carbonylethyl]phorbin.iodide in the form of dark brown crystals. Yield of 71.7%.

IR absorption spectrum (KBr, cm$^{-1}$): 3490, 2950, 2910, 2850, 1730, 1695, 1615.

EXAMPLES 15 to 20

The compounds as produced in Examples 2, 4, 5, 6, 10 and 13 are treated with methyl iodide, respectively, in the same manner as described in Example 14 to give the following compounds:

EXAMPLE 15

2-Ethenyl-4-ethyl-1,3,5,8-tetramethyl-9-desoxo-9-hydroxy-10-methoxycarbonyl-7-[2-(2-trimethylammonioethyloxy)carbonylethyl]-phorbin.iodide. Dark green crystals in yield of 77.2%.

Ir absorption spectrum (KBr, cm$^{-1}$): 3390, 2950, 2920, 2850, 1730, 1615.

EXAMPLE 16

2-Ethenyl-4-ethyl-1,3,5,8-tetramethyl-9-desoxo-9-hydroxy-10-methoxycarbonyl-7-[2-(2-trimethylammoniopropyloxy)carbonylethyl]-phorbin.iodide. Dark green crystals in yield of 69.3%.

IR absorption spectrum (kBr, cm$^{-1}$): 3390, 2950, 2920, 2810, 1730, 1615.

EXAMPLE 17

2-Ethenyl-4-ethyl-1,3,5,8-tetramethyl-9-oxo-10-desmethoxycarbonyl-10(2H)-7-[2-(2-trimethylammonioethyloxy)carbonylethylphorbin.iodide. Black crystals in yield of 56.0%.

EXAMPLE 18

2-Ethenyl-4-ethyl-1,3,5,8-tetramethyl-9-desoxo-9-hydroxy-10-desmethoxycarbonyl-10(2H)-7-[2-(2-trimethylamminoethyloxy)carbonylethyl]-phorbin.iodide. Dark green crystals in yield of 64.5%.

Ir Absorption spectrum (KBr. cm$^{-1}$): 3395, 2955, 2920, 2860, 1735, 1620.

EXAMPLE 19

2-Desethenyl-2-(1-methoxyethyl)-4-ethyl-1,3,5,8-tetramethyl-9-desoxo-9-hdyroxy-1-methoxycarbonyl-7[2-(2-trimethylammonioethyloxy)carbonylethyl]-phorbin-.iodide. Dark green crystals in yield of 54.3%.

EXAMPLE 20

2-Desethenyl-2-(1-(2-(2-hydroxyethyloxy)ethyloxy)ethyl)-4-ethyl-1,3,5,8-tetramethyl-9-oxo-10-desmethoxycarbonyl-10(2H)-7-[2-(2-trimethylammonioethyloxy)-carbonylethyl]-phorbin. iodide. Black crystals in yield of 50.6%.

IR Absorption spectrum (KBr, cm$^{-1}$): 3390, 2950, 2920, 2860, 1735, 1690, 1620.

We claim:

1. A pheophorbide derivative of the general formula:

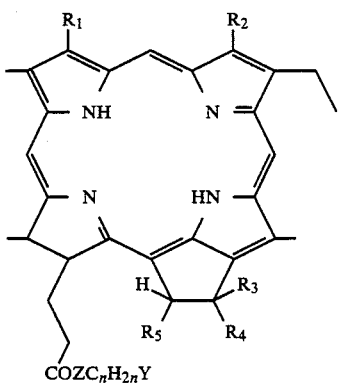

wherein Z is O or NH; n is an integer of 1 to 6; Y is NR'R'' or

wherein R', R'' and R''' are the same or different or each represents a $C_1$ to $C_4$ lower alkyl group; $X^-$ is a halogen or organic acid ion; $R_1$ is an ethenyl group, $C_1$ to $C_4$ lower alkyl group or

wherein m is an integer of 0 to 6; $R_6$ is H or a $C_1$ to $C_4$ lower alkyl group; $R_2$ is $CH_3$, CHO or $CH_2OH$; either of $R_3$ and $R_4$ is H, with the other being OH, or both of them combine to represent =O; $R_5$ is H or $CO_2CH_3$.

2. A derivative according to claim 1 wherein $R_1$, R', R'', R''' or $R_6$ is independently methyl, ethyl or propyl group, and $X^-$ is Cl, Br, I, acetic acid or p-toluenesulfonic acid ion.

3. An agent for detecting cancer tissue by the specific emission of fluorescence under the irradiation of light, which comprises a compound of the general formula:

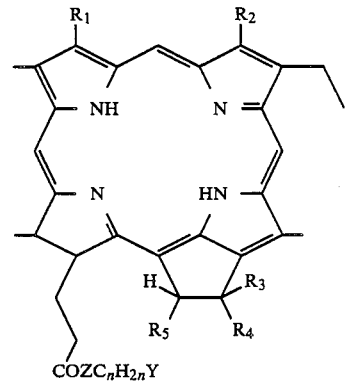

wherein Z is O or NH; n is an integer of 1 to 6; Y is NR'R'' or

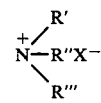

wherein R', R'' and R''' are the same or different or each represents a $C_1$ to $C_4$ lower alkyl group; $X^-$ is a halogen or organic acid ion; $R_1$ is an ethenyl group, $C_1$ to $C_4$ lower alkyl group or

wherein m is an integer of 0 to 6; $R_6$ is H or a $C_1$ to $C_4$ lower alkyl group; $R_2$ is $CH_3$, CHO or $CH_2OH$; either of $R_3$ and $R_4$ is H, with the other being OH, or both of them combine to represent =O; $R_5$ is H or $CO_2CH_3$.

4. A method of marking cancer tissue, which comprises administering a compound of the general formula:

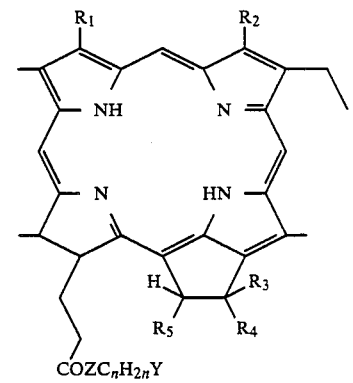

wherein Z is O or NH; n is an integer of 1 to 6; Y is NR'R'' or

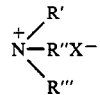

wherein R', R'' and R''' are the same or different or each represents a $C_1$ to $C_4$ lower alkyl group; $X^-$ is a halogen or organic acid ion; $R_1$ is an ethenyl group, $C_1$ to $C_4$ lower alkyl group or

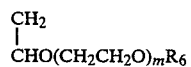

wherein m is an integer of 0 to 6; $R_6$ is H or a $C_1$ to $C_4$ lower alkyl group); $R_2$ is $CH_3$, CHO or $CH_2OH$; either of $R_3$ and $R_4$ is H, with the other being OH, or both of them combine to represent =O; $R_5$ is H or $CO_2CH_3$ to a cancer-carrying subject, whereby cancer tissue is made to specifically emit fluorescence under irradiation of light.

* * * * *

UNITED STATES PATENT AND TRADEMARK OFFICE
CERTIFICATE OF CORRECTION

PATENT NO. : 4,965,064

DATED : October 23, 1990

INVENTOR(S) : Michito Karasawa, et al.

It is certified that error appears in the above-identified patent and that said Letters Patent is hereby corrected as shown below:

ON THE TITLE PAGE
In the Abstract, line 11 from the bottom;

Column 13, line 53;

Column 14, line 32; and

Column 15, line 5;

that portion of the formula reading

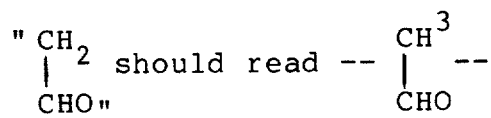

Column 1, line 41: "Prophyrins" should read --Porphyrins-- lines 48 and 54: "HP" should read --HpD--

Column 3, line 40: under the formula insert --(3)-- line 41; insert the following:

UNITED STATES PATENT AND TRADEMARK OFFICE
CERTIFICATE OF CORRECTION

PATENT NO. : 4,965,064
DATED : October 23, 1990
INVENTOR(S) : Michito Karasawa, et al It is certified that error appears in the above-identified patent and that said Letters Patent is hereby corrected as shown below:

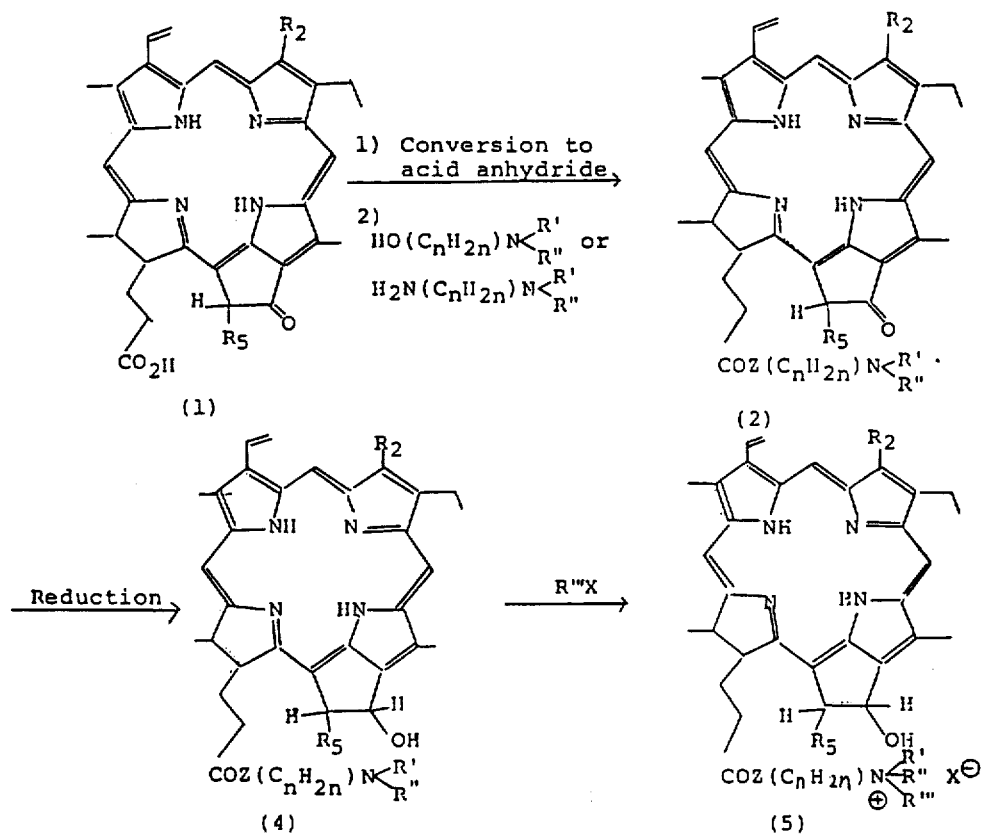

UNITED STATES PATENT AND TRADEMARK OFFICE
CERTIFICATE OF CORRECTION

PATENT NO. : 4,965,064
DATED : October 23, 1990
INVENTOR(S) : Michito Karasawa, et al It is certified that error appears in the above-identified patent and that said Letters Patent is hereby corrected as shown below:

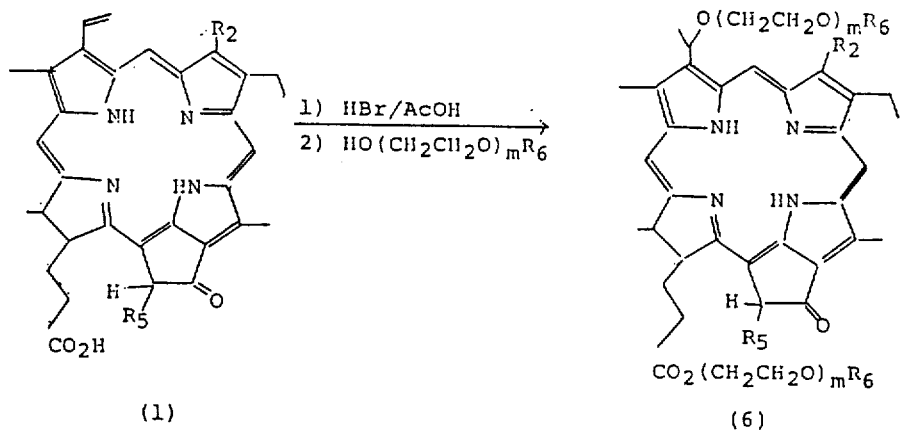

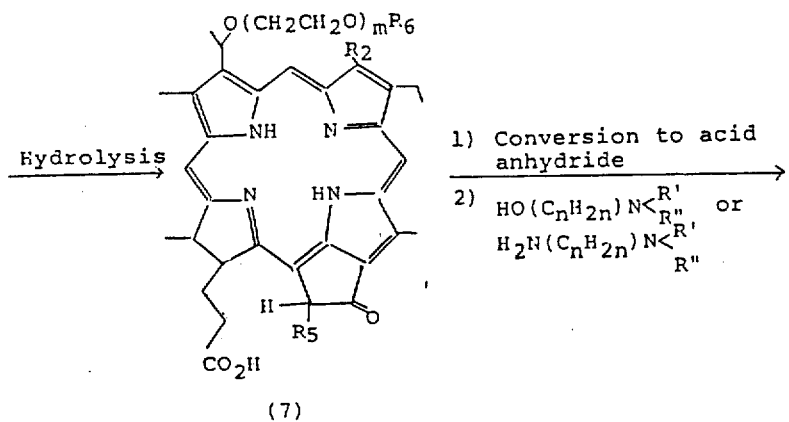

UNITED STATES PATENT AND TRADEMARK OFFICE
CERTIFICATE OF CORRECTION

PATENT NO.   :  4,965,064

DATED        :  October 23, 1990

INVENTOR(S)  :  Michito Karasawa, et al.

It is certified that error appears in the above-identified patent and that said Letters Patent is hereby corrected as shown below:

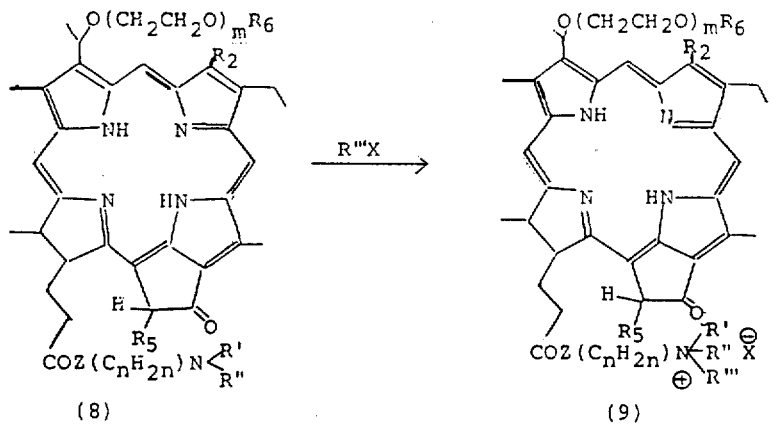

Column 5, line 6: delete "or"

line 10: delete the formula

Column 6, line 28: "diganosis" should read --diagnosis-- line 40: that portion of the chemical name reading "(2-trimethylammonio-" should read --3-trimethylammonio---

Column 7, line 49: that portion of the chemical name reading "9-desoxy-9-" should read --9-desoxo-9- --

Column 10, line 59: that portion of the chemical name

UNITED STATES PATENT AND TRADEMARK OFFICE
CERTIFICATE OF CORRECTION

PATENT NO. : 4,965,064
DATED : October 23, 1990
INVENTOR(S) : Michito Karasawa, et al.

It is certified that error appears in the above-identified patent and that said Letters Patent is hereby corrected as shown below:

reading "(1-1-methoxyethyl) should read --(1-methoxyethyl)--

Column 11, line 14: that portion of the chemical name reading "(1-2(2-hydroxyethyloxy)" should read --(1-(2-hydroxyethyloxy)-- line 20: that portion of the chemical name reading "7-propinionic" should read --7-propionic-- line 40: that portion of the chemical name reading "2-desethnyl" should read --2-desethenyl-- line 46: that portion of the chemical name reading "ethyloxy)ethyloxy)ethyl)4-" should read --ethyloxy)ethyl)-4- -- line 52: that portion of the chemical name reading "7-proppionic acid" should read --7-propionic acid-- line 63: that portion of the chemical name reading "1,2-desethenyl" should read --1,$\Delta$2-desethenyl--

Column 12, line 1: "(2-diemthylaminoethyloxy)" should read --(2-dimethylaminoethyloxy)--

UNITED STATES PATENT AND TRADEMARK OFFICE
CERTIFICATE OF CORRECTION

PATENT NO. : 4,965,064
DATED : October 23, 1990
INVENTOR(S) : Michito Karasawa, et al.

It is certified that error appears in the above-identified patent and that said Letters Patent is hereby corrected as shown below:

Column 12, line 16: "(2-(-trimethylammonioethyloxy)" should read --(2-(trimethylammonioethyloxy)-- line 18: "benzne" should read --benzene-- line 21: "produced" should read --produced in-- line 49: that portion of the chemical name reading "(2-trimethylam-" should read --(3-trimethylam- -- line 64: that portion of the chemical name reading "thylamminoethyloxy)" should read --thylammonioethyloxy)-- line 67: "Ir" should read --IR--

UNITED STATES PATENT AND TRADEMARK OFFICE
CERTIFICATE OF CORRECTION

PATENT NO. : 4,965,064

DATED : October 23, 1990

INVENTOR(S) : Michito Karasawa, et al.

It is certified that error appears in the above-identified patent and that said Letters Patent is hereby corrected as shown below:

Column 13, line 4: that portion of the chemical name reading "9-hdyroxy-1-methoxycarbonyl-7[2-" should read --9-hydroxy-10-methoxycarbonyl-7-[2- --

Signed and Sealed this

Sixteenth Day of March, 1993

Attest:

STEPHEN G. KUNIN

Attesting Officer

Acting Commissioner of Patents and Trademarks